Figure 1:
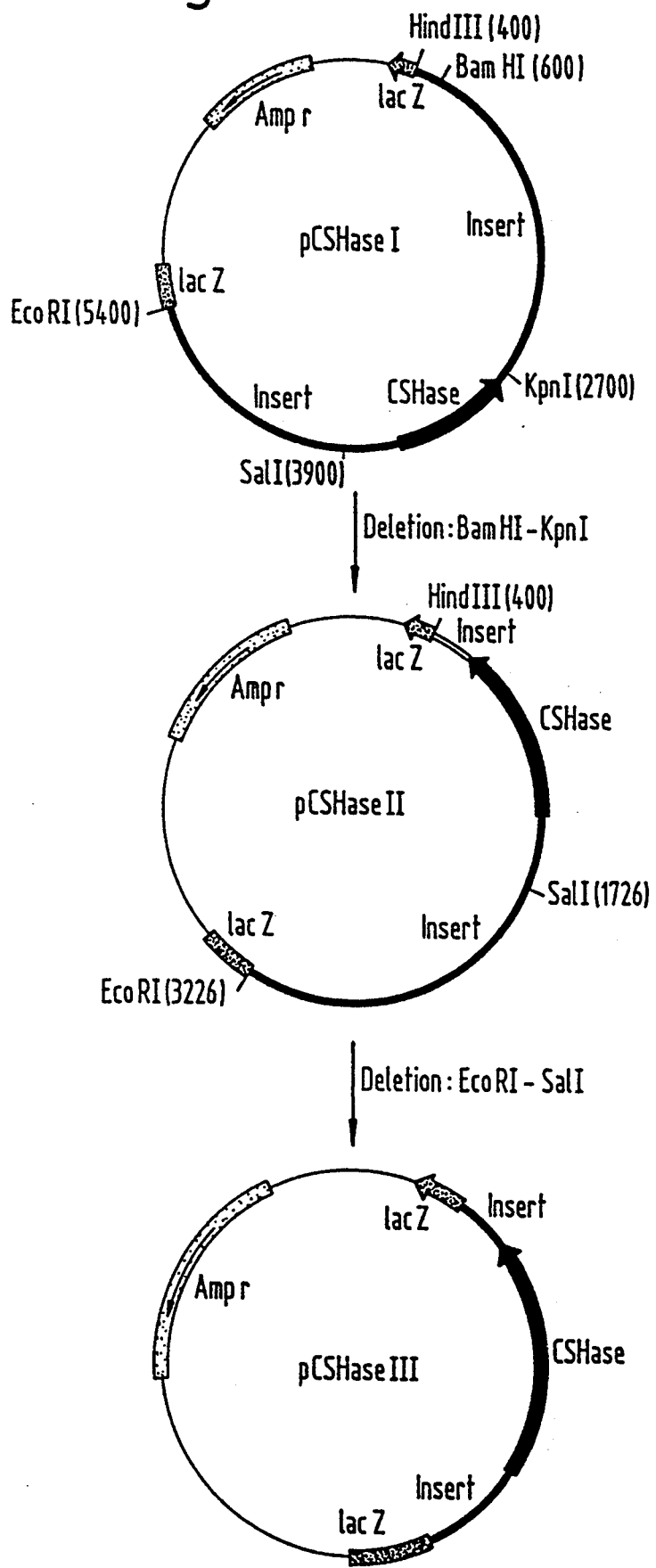

United States Patent [19]

Burtscher et al.

[11] Patent Number: 5,416,014

[45] Date of Patent: May 16, 1995

[54] CLONED N-CARBAMOYL SARCOSINE AMIDOHYDROLASE

[75] Inventors: Helmut Burtscher, Habach; Günther Schumacher, Bernried, both of Germany

[73] Assignee: Boehringer Mannheim GmbH, Germany

[21] Appl. No.: 107,042

[22] Filed: Aug. 17, 1993

Related U.S. Application Data

[62] Division of Ser. No. 762,131, Sep. 19, 1991, abandoned.

[30] Foreign Application Priority Data

Sep. 20, 1990 [DE] Germany .................. 40 29 844.2

[51] Int. Cl.[6] ............... C12N 15/55; C12N 9/80; C12N 15/70; C12N 1/21
[52] U.S. Cl. ................. 435/228; 435/69.1; 435/71.2; 435/252.3; 435/252.33; 435/320.1; 435/830; 435/849; 935/14; 935/29; 935/56; 935/73; 536/23.2
[58] Field of Search .............. 435/69.1, 71.2, 228, 435/252.3, 252.33, 320.1, 830, 849; 935/14, 29, 56, 73; 536/23.2

[56] References Cited

U.S. PATENT DOCUMENTS

| | | | |
|---|---|---|---|
| 4,464,473 | 8/1984 | Orser et al. | 435/172.3 |
| 4,469,791 | 9/1984 | Colson et al. | 435/252.31 |
| 4,472,502 | 9/1984 | Snow et al. | 435/172.3 |
| 4,645,739 | 2/1987 | Deeg et al. | 435/25 |
| 4,816,393 | 3/1989 | Siedel et al. | 435/18 |

FOREIGN PATENT DOCUMENTS

| | | |
|---|---|---|
| 0112571A1 | 7/1984 | European Pat. Off. . |
| 0154269A3 | 9/1985 | European Pat. Off. . |
| 0437254A2 | 7/1991 | European Pat. Off. . |

OTHER PUBLICATIONS

Chemical Abstract, vol. 109, No. 11, Sep. 12, 1988, Columbus, Ohio abstract No. 89041D, Siedel, J. et al.: 'Fully enzymatic colorimetric assay of serum and urine creatinine which obviates the need for sample blank measurements' Seite 344.

Shimizu et al, "Evaluation of two alternative metabolic ..." Arch. Microbiol 145:322–328 (1986).

J. Futterer et al. "The Instability of a Recombinant Plasmid ..." Gene 67(1) 141–145 (Jul. 15, 1988).

J. Sambrook et al. "Molecular Cloning: A Laboratory Manual", 2nd edition Cold Spring Harbor Laboratory Press, Chapters 1 & 17 (Oct. 16, 1989).

*Primary Examiner*—Robert A. Wax
*Assistant Examiner*—Rebecca Prouty
*Attorney, Agent, or Firm*—Nikaido, Marmelstein, Murray & Oram

[57] ABSTRACT

The invention concerns a recombinant DNA which contains
  (1) the sequence shown in SEQ ID NO: 1,
  (2) a sequence corresponding to this sequence within the scope of the degeneracy of the genetic code or
  (3) a sequence which hybridizes with a sequence from (1) or/and (2) under stringent hybridizing conditions whereby the DNA sequence codes for a protein with N-carbamoyl sarcosine amidohydrolase activity.

Furthermore the invention concerns a recombinant vector with the DNA according to the present invention as well as a process for the isolation of a recombinant protein with N-carbamoyl sarcosine amidohydrolase activity and its use for the determination of creatinine.

17 Claims, 3 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 795 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..795

( x i ) SEQUENCE DESCRIPTION: SEQ ID NO:1:

```
ATG ACT GAA ACA TCG GGA ACC TTC AAC GAC ATT GAA GCT CGA CTA GCC        48
Met Thr Glu Thr Ser Gly Thr Phe Asn Asp Ile Glu Ala Arg Leu Ala
 1               5                  10                  15

GCT GTG CTG GAA GAA GCA TTC GAA GCC GGC ACG AGC ATC TAC AAC GAG        96
Ala Val Leu Glu Glu Ala Phe Glu Ala Gly Thr Ser Ile Tyr Asn Glu
            20                  25                  30

CGC GGT TTC AAG CGT CGA ATC GGC TAC GGC AAC CGT CCC GCC GTC ATC       144
Arg Gly Phe Lys Arg Arg Ile Gly Tyr Gly Asn Arg Pro Ala Val Ile
        35                  40                  45

CAT ATC GAC CTC GCT AAC GCA TGG ACT CAA CCC GGG CAC CCC TTC AGC       192
His Ile Asp Leu Ala Asn Ala Trp Thr Gln Pro Gly His Pro Phe Ser
    50                  55                  60
```

| | | | | | | | | | | | | | | | | |
|---|---|---|---|---|---|---|---|---|---|---|---|---|---|---|---|---|
| TGC | CCG | GGC | ATG | GAG | ACG | ATC | ATC | CCG | AAC | GTG | CAG | CGG | ATC | AAC | GAA | 240 |
| Cys | Pro | Gly | Met | Glu | Thr | Ile | Ile | Pro | Asn | Val | Gln | Arg | Ile | Asn | Glu | |
| 65 | | | | 70 | | | | | 75 | | | | | 80 | | |
| GCT | GCA | CGC | GCC | AAA | GGG | GTC | CCG | GTC | TTC | TAC | ACC | ACC | AAC | GTG | TAC | 288 |
| Ala | Ala | Arg | Ala | Lys | Gly | Val | Pro | Val | Phe | Tyr | Thr | Thr | Asn | Val | Tyr | |
| | | | | 85 | | | | | 90 | | | | | 95 | | |
| CGG | AAT | CGC | GAT | GCC | AGC | TCC | GGG | ACC | AAC | GAT | ATG | GGC | CTG | TGG | TAC | 336 |
| Arg | Asn | Arg | Asp | Ala | Ser | Ser | Gly | Thr | Asn | Asp | Met | Gly | Leu | Trp | Tyr | |
| | | | 100 | | | | | 105 | | | | | 110 | | | |
| TCG | AAG | ATC | CCC | ACC | GAA | ACC | CTG | CCG | GCA | GAC | TCC | TAC | TGG | GCG | CAG | 384 |
| Ser | Lys | Ile | Pro | Thr | Glu | Thr | Leu | Pro | Ala | Asp | Ser | Tyr | Trp | Ala | Gln | |
| | | 115 | | | | | 120 | | | | | 125 | | | | |
| ATC | GAT | GAC | CGC | ATC | GCC | CCC | GCA | GAT | GGT | GAA | GTC | GTG | ATC | GAG | AAA | 432 |
| Ile | Asp | Asp | Arg | Ile | Ala | Pro | Ala | Asp | Gly | Glu | Val | Val | Ile | Glu | Lys | |
| | 130 | | | | | 135 | | | | | 140 | | | | | |
| AAC | CGT | GCC | TCG | GCA | TTC | CCG | GGA | ACG | AAT | TTG | GAG | CTC | TTC | CTG | ACG | 480 |
| Asn | Arg | Ala | Ser | Ala | Phe | Pro | Gly | Thr | Asn | Leu | Glu | Leu | Phe | Leu | Thr | |
| 145 | | | | | 150 | | | | | 155 | | | | | 160 | |
| TCC | AAC | CGC | ATC | GAC | ACC | CTC | ATC | GTG | ACC | GGG | GCA | ACC | GCG | GCA | GGC | 528 |
| Ser | Asn | Arg | Ile | Asp | Thr | Leu | Ile | Val | Thr | Gly | Ala | Thr | Ala | Ala | Gly | |
| | | | | 165 | | | | | 170 | | | | | 175 | | |
| TGC | GTG | CGC | CAC | ACT | GTC | GAG | TAC | GCA | ATC | GCC | AAG | GGA | TTC | CGC | CCG | 576 |
| Cys | Val | Arg | His | Thr | Val | Glu | Tyr | Ala | Ile | Ala | Lys | Gly | Phe | Arg | Pro | |
| | | | 180 | | | | | 185 | | | | | 190 | | | |
| ATC | ATT | CCA | CGC | GAA | ACC | ATC | GGC | GAC | CGC | GTG | CCA | GGT | GTT | GTG | CAG | 624 |
| Ile | Ile | Pro | Arg | Glu | Thr | Ile | Gly | Asp | Arg | Val | Pro | Gly | Val | Val | Gln | |
| | | 195 | | | | | 200 | | | | | 205 | | | | |
| TGG | AAC | CTT | TAC | GAC | ATC | GAC | AAC | AAG | TTT | GGT | GAC | GTG | GAG | TCT | ACC | 672 |
| Trp | Asn | Leu | Tyr | Asp | Ile | Asp | Asn | Lys | Phe | Gly | Asp | Val | Glu | Ser | Thr | |
| 210 | | | | | 215 | | | | | 220 | | | | | | |
| GAT | TCG | GTG | GTG | CAA | TAC | TTG | TAC | GCA | CTT | CCG | CAG | TTC | GAA | GAC | ACC | 720 |
| Asp | Ser | Val | Val | Gln | Tyr | Leu | Tyr | Ala | Leu | Pro | Gln | Phe | Glu | Asp | Thr | |
| 225 | | | | | 230 | | | | | 235 | | | | | 240 | |
| GTT | CCG | AAG | ACC | CTA | TCC | GAT | CCC | CAG | CCT | GAG | GTA | GAG | GCT | CCG | GCA | 768 |
| Val | Pro | Lys | Thr | Leu | Ser | Asp | Pro | Gln | Pro | Glu | Val | Glu | Ala | Pro | Ala | |
| | | | | 245 | | | | | 250 | | | | | 255 | | |
| GAC | CCG | GTC | TTC | GCT | GAG | CAG | CAC | TAA | | | | | | | | 795 |
| Asp | Pro | Val | Phe | Ala | Glu | Gln | His | | | | | | | | | |
| | | | 260 | | | | 265 | | | | | | | | | |

( 2 ) INFORMATION FOR SEQ ID NO:2:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Thr | Glu | Thr | Ser | Gly | Thr | Phe | Asn | Asp | Ile | Glu | Ala | Arg | Leu | Ala |
| 1 | | | | 5 | | | | | 10 | | | | | 15 | |
| Ala | Val | Leu | Glu | Glu | Ala | Phe | Glu | Ala | Gly | Thr | Ser | Ile | Tyr | Asn | Glu |
| | | | 20 | | | | | 25 | | | | | 30 | | |
| Arg | Gly | Phe | Lys | Arg | Arg | Ile | Gly | Tyr | Gly | Asn | Arg | Pro | Ala | Val | Ile |
| | | 35 | | | | | 40 | | | | | 45 | | | |
| His | Ile | Asp | Leu | Ala | Asn | Ala | Trp | Thr | Gln | Pro | Gly | His | Pro | Phe | Ser |
| | 50 | | | | | 55 | | | | | 60 | | | | |
| Cys | Pro | Gly | Met | Glu | Thr | Ile | Ile | Pro | Asn | Val | Gln | Arg | Ile | Asn | Glu |
| 65 | | | | 70 | | | | | 75 | | | | | 80 | |
| Ala | Ala | Arg | Ala | Lys | Gly | Val | Pro | Val | Phe | Tyr | Thr | Thr | Asn | Val | Tyr |
| | | | | 85 | | | | | 90 | | | | | 95 | |

```
Arg Asn Arg Asp Ala Ser Ser Gly Thr Asn Asp Met Gly Leu Trp Tyr
        100                 105                 110

Ser Lys Ile Pro Thr Glu Thr Leu Pro Ala Asp Ser Tyr Trp Ala Gln
        115                 120                 125

Ile Asp Asp Arg Ile Ala Pro Ala Asp Gly Glu Val Val Ile Glu Lys
        130             135                 140

Asn Arg Ala Ser Ala Phe Pro Gly Thr Asn Leu Glu Leu Phe Leu Thr
145                 150                 155                 160

Ser Asn Arg Ile Asp Thr Leu Ile Val Thr Gly Ala Thr Ala Ala Gly
                165                 170                 175

Cys Val Arg His Thr Val Glu Tyr Ala Ile Ala Lys Gly Phe Arg Pro
            180                 185                 190

Ile Ile Pro Arg Glu Thr Ile Gly Asp Arg Val Pro Gly Val Val Gln
        195                 200                 205

Trp Asn Leu Tyr Asp Ile Asp Asn Lys Phe Gly Asp Val Glu Ser Thr
        210             215                 220

Asp Ser Val Val Gln Tyr Leu Tyr Ala Leu Pro Gln Phe Glu Asp Thr
225                 230                 235                 240

Val Pro Lys Thr Leu Ser Asp Pro Gln Pro Glu Val Glu Ala Pro Ala
                245                 250                 255

Asp Pro Val Phe Ala Glu Gln His
                260
```

( 2 ) INFORMATION FOR SEQ ID NO:3:

( i ) SEQUENCE CHARACTERISTICS:
        ( A ) LENGTH: 373 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GTCGACATCC AGCAGATCTG GCATCTGATA CGAACAGCGC CGCTTGAGCA CTCGGTACTA      60
CTTTTTGAAC CGCTAGATAT CTTAGTTTTC AAATACTGCC AGAGGGAACT CCCTACCCCA     120
TGGCAACCAT CTTTACTGCT GGTCATGACG CGCATGGATT CGCTCAAATG GGTCACAGCT     180
TGCTGCCATC CGAGAGCTAG AAGCCGTAAT TTCCCAGCGG TTTTTGAATT ATTCGCATCT     240
CGACAAGGCC TTTTACTAAC AAAAAATATC TTTTCCCGAA CCACTAGTGC CTCAGCAATC     300
CTGGGCTATA GYACTTACCA GAGCAACGAG GTTGCTTTAT CAGCAACAAA CCAAGATGAG     360
AATAGAGAGA GCA                                                       373
```

CLONED N-CARBAMOYL SARCOSINE AMIDOHYDROLASE

This application is division of application Ser. No. 07/762,131 filed Sept. 19, 1991, now abandoned.

The enzyme N-carbamoyl sarcosine amidohydrolase (CSHase) is required for the determination of the content of creatinine in liquids. Creatinine is an important parameter for kidney diagnostics. Annually about one thousand million tests are carried out worldwide. Therefore the provision of the enzyme CSHase at a low cost, as well as the ability to carry out the fermentation without problems are basic requirements for the production of a diagnostic kit for the determination of creatinine.

CSHase is a protein with a molecular weight of ca. 35 kD (subunit), a $K_M$ of $3 \times 10^{-3}$ mol/l and a specific activity of 2 U/mg. CSHase (EC 3.5.1.59) has up to now been isolated from Arthrobacter. The complex nutrient requirements of Arthrobacter and the low enzyme activities of 100 to 200 U/l obtained during the enrichment are a disadvantage of this process.

The object of the present invention was therefore to eliminate some of the disadvantages of the state of the art by providing an improved enrichment process for CSHase.

The present invention provides a recombinant DNA which contains (1) the sequence shown in SEQ ID NO: 1,
(2) a sequence corresponding to it within the scope of the degeneracy of the genetic code or
(3) a sequence which hybridizes with a sequence from (1) or/and (2) under stringent hybridizing conditions whereby the DNA sequence codes for a protein with N-carbamoyl sarcosine amidohydrolase activity.

The DNA according to the present invention shown in SEQ ID NO: 1 codes for a protein with N-carbamoyl sarcosine activity which has the amino acid sequence shown in SEQ ID NO:2. In addition the present invention also encompasses a DNA sequence which corresponds to the sequence shown in SEQ ID NO: 1 within the scope of the degeneracy of the genetic code, in which the modifications should preferably result in an improved codon usage in the respective host organism used, in particular in E.coli. The suitable codon usage for the individual host organisms is known to one skilled in the art.

Furthermore the invention encompasses a DNA sequence which, under stringent hybridizing conditions, hybridizes with the sequence shown in SEQ ID NO:1 or/and a sequence derived therefrom within the scope of the degeneracy of the genetic code. Within the scope of the present invention the term "to hybridize under stringent conditions" is understood to mean that a hybridization signal occurs even after washing at a high temperature, in particular at 65° C., or/and in a buffer with low salt content (cf. also Maniatis et al., "Molecular Cloning. A laboratory manual"(1982), Cold Spring Harbor Laboratory, New York).

A protein with N-carbamoyl sarcosine amidohydrolase activity within the sense of the present invention is understood as the amino acid sequence shown in SEQ ID NO:2 and also its variants and derivatives which are obtained by deletion, insertion or/and substitution of individual amino acids as well as by binding to one or several other polypeptide domains (resulting in a fusion protein).

The recombinant DNA according to the present invention is obtained by cloning Arthrobacter DNA fragments in a host organism, preferably E.coli, and selecting the clones thus obtained for direct gene expression. It is expedient to identify the clones which code for CSHase by means of a plate activity test. For this sarcosine oxidase, peroxidase, N-carbamoyl sarcosine, 4-aminoantipyrine and tribromo-3-hydroxybenzoic acid in phosphate buffered agarose is added to the medium. The principle of the measurement is as follows: The CSHase expressed by a positive clone converts added N-carbamoyl sarcosine to sarcosine, this is degraded by sarcosine oxidase to glycine, formaldehyde and hydrogen peroxide. The peroxidase uses the hydrogen peroxide which forms to convert the added colour substrate into a dark-violet dye by oxidative coupling. By this means positive clones can be identified by the colouration.

The present invention thus also provides a recombinant vector which contains at least one copy of a recombinant DNA as claimed in claim 1 as a heterologous insertion. The vector according to the present invention can be a eukaryotic or prokaryotic vector or a vector which can be expressed in eukaryotes as well as in prokaryotes. It is preferably a prokaryotic vector.

The vector according to the present invention can in addition be a vector which is present extrachromosomally in a host cell or is integrated into the chromosome of the host cell. An example of a vector which is integrated into the genome of the host cell is for example a bacteriophage λ vector in an E.coli cell. A plasmid is an example of a vector which is present extrachromosomally. The vector according to the present invention is preferably a plasmid.

The expression of CSHase by means of a 5 kb long Arthrobacter DNA fragment cloned in E.coli proved to be extremely unstable. Even after 24 hours there was no detectable expression of CSHase in the originally positive clones. It, however, surprisingly turned out that after shortening the Arthrobacter DNA fragment to a length of 1.3 kb the instability could be eliminated. The length of the heterologous insertion in a recombinant vector according to the present invention is therefore not more than 1.3 kb long.

The heterologous insertion on a recombinant vector according to the present invention is preferably under the control of an expression signal in order to allow expression of CSHase in a host organism which has been transformed by a vector according to the present invention. This expression signal must be suitable for the host organism used in each case. For this an inducible expression signal is on the one hand suitable for the particular preferred expression in E.coli. The well-known inducible E.coli promoters lac, tac or trp can for example be used or the Salmonella promoter mgl (WO 88/09373) can preferably be used which is an expression signal which is heterologous with regard to the E.coli vector.

On the other hand it surprisingly turned out that an expression signal has also proven to be suitable which is homologous to the insertion i.e. an expression signal derived from Arthrobacter. The authentic promoter of the N-carbamoyl sarcosine amidohydrolase gene or a sequence derived therefrom which has a surprisingly high activity in E.coli is particularly preferably used for this.

This promoter region is located on a 373 base pair DNA fragment which is shown in SEQ ID NO:3. It was found that not only this 373 bp fragment but also shortened fragments or fragments derived therefrom have promoter properties.

The present invention also provides a cell which is transformed with a DNA according to the present invention or with a recombinant vector according to the present invention. This cell is preferably a bacterial cell, particularly preferably an E.coli cell.

The present invention also provides a process for the isolation of a protein with N-carbamoyl sarcosine amidohydrolase activity in which (1) a host cell is transformed with a DNA according to the present invention or with a vector according to the present invention whereby a transformed host cell is formed which contains at least one copy of the N-carbamoyl sarcosine amidohydrolase gene, (2) transformed host cells are cultured in a suitable medium, (3) the N-carbamoyl sarcosine amidohydrolase gene is expressed in the transformed host cells and (4) the expression product is isolated from the medium or the host cells.

The transformation of the host cell and the culture of the transformed host cells can be carried out by a person skilled in the art according to well-known methods in the field of molecular biology. The expression of the N-carbamoyl sarcosine amidohydrolase gene in the transformed host cells is carried out by an induction step if an inducible expression signal is used or it is carried out constitutively. The expression product is preferably isolated from the medium or the host cells by means of DEAE Sephadex and phenyl-Sepharose chromatography with subsequent ammonium sulphate precipitation as described e.g. in EP-A 0 112 571 Example 2b.

E.coli bacteria are preferably used as the host cells for the process according to the present invention. Furthermore it is preferred to use a vector in which the heterologous insertion containing the N-carbamoyl sarcosine amidohydrolase gene is not longer than 1.3 kb. Particularly preferred is the use of a vector in which the expression of the N-carbamoyl sarcosine amidohydrolase gene is under the control of the authentic promoter or a sequence derived therefrom. pBMP62 (FIG. 3) is an example of such a vector.

The present invention also provides the protein with N-carbamoyl sarcosine activity which is obtained by the process according to the present invention. Such a protein preferably has the amino acid sequence shown in SEQ ID NO:2. Derivatives and variants of this protein can also be obtained by the process according to the present invention.

Furthermore the present invention also encompasses the use of the protein according to the present invention for the determination of creatinine as well as a reagent for the determination of creatinine which contains the protein according to the present invention with N-carbamoyl sarcosine amidohydrolase activity.

Figure 2:
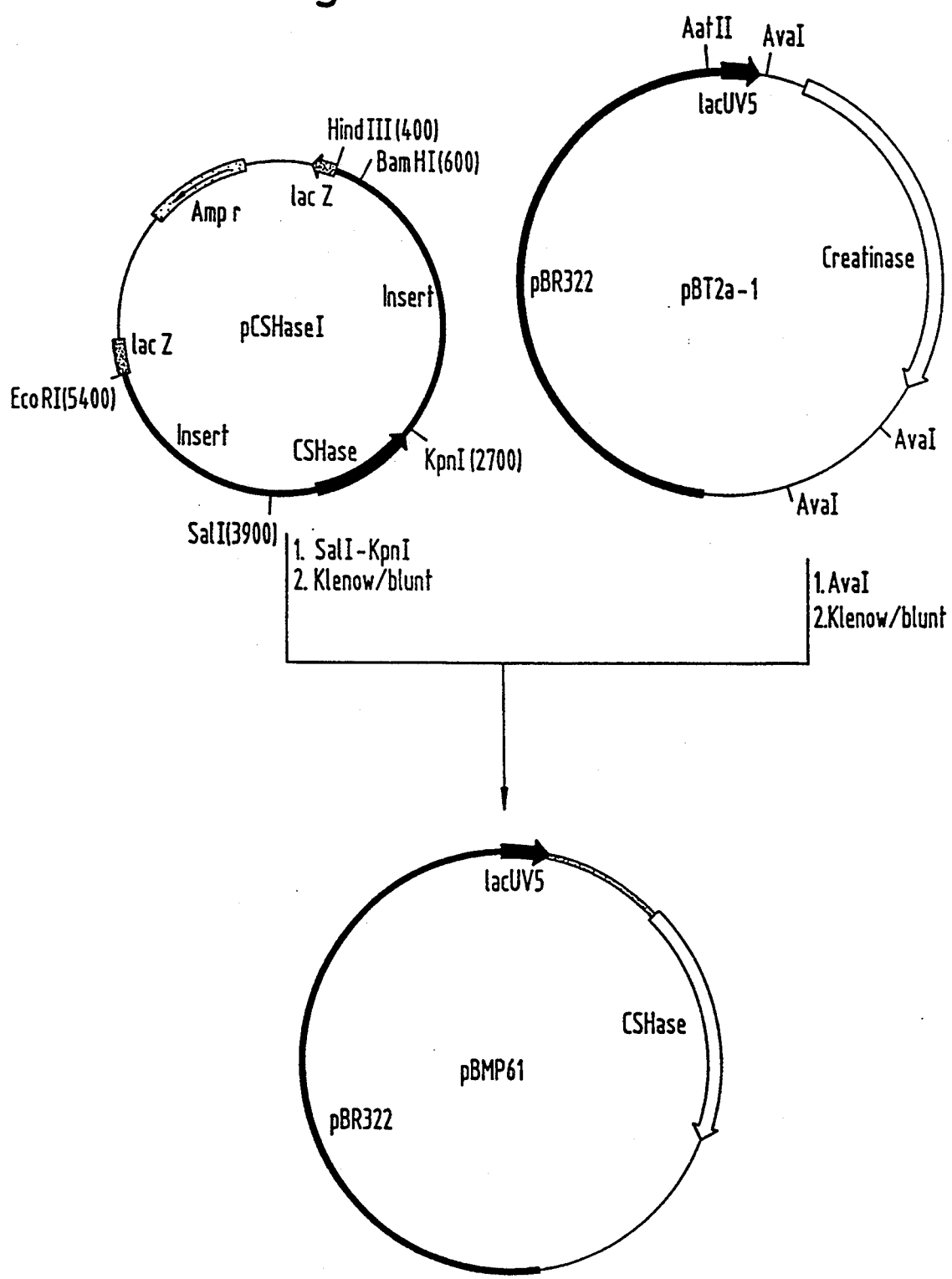
Figure 3:
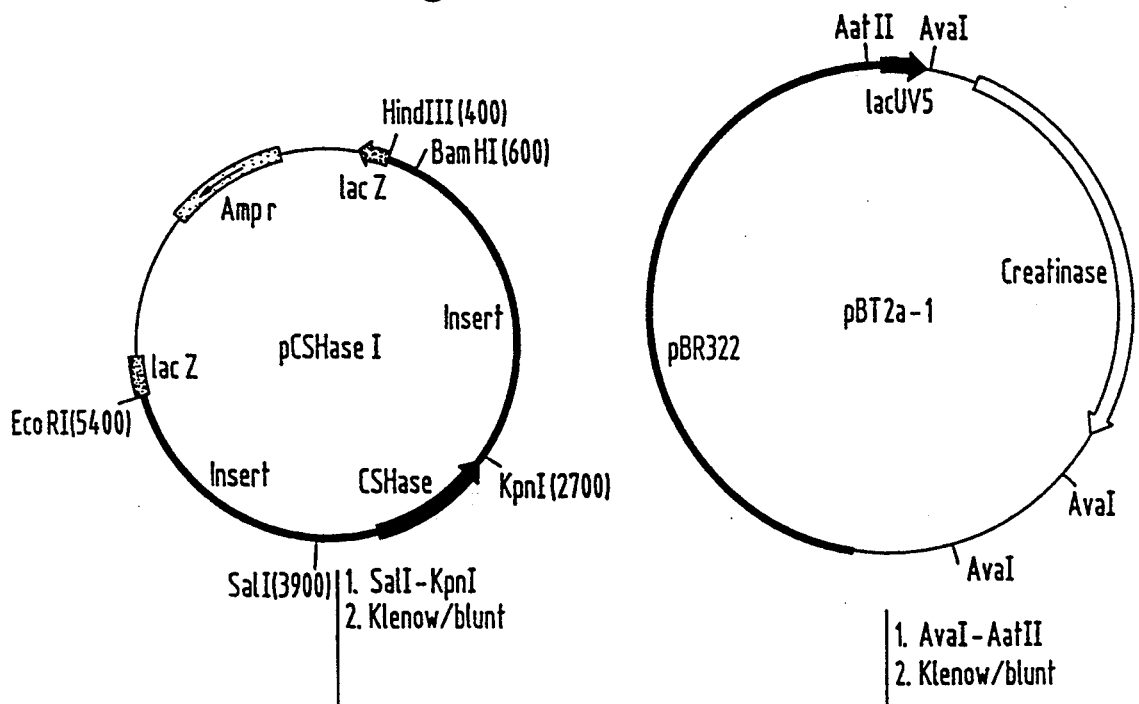
Figure 3:
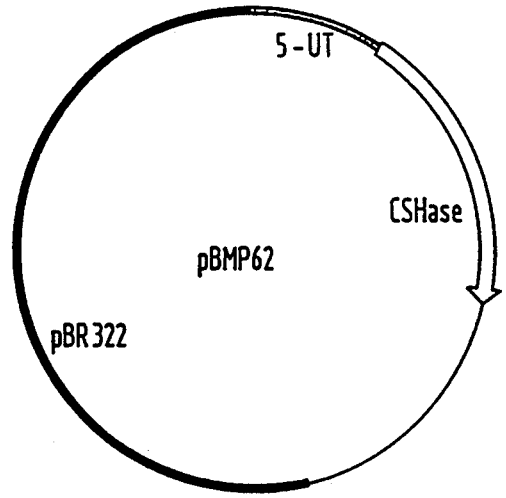

The following examples are intended to further elucidate the invention in conjunction with the sequence protocols and FIGS. 1 to 3.

SEQ ID NO: 1 shows the DNA sequence of the CSHase gene,

SEQ ID NO: 2 shows the amino acid sequence of the CSHase,

SEQ ID NO: 3 shows the DNA fragment which acts as a promoter for the CSHase gene, FIG. 1 shows the construction of the stable plasmid pCSHaseIII formed from pCSHaseI by deletion, FIG. 2 shows the construction of the expression vector pBMP61, FIG. 3 shows the construction of the expression vector pBMP62.

The microorganisms and plasmids mentioned in the description and in the examples

| Arthrobacter spec. | DSM 2563 |
| E.coli ED 8654 | DSM 2102 |
| pBT 2a-1 | DSM 3148p | are deposited in the German Collection for Microorganisms and Cell Cultures GmbH (DSM), Mascheroder Weg 1B, D-3300 Braunschweig.

EXAMPLE 1

Identification of positive clones

DNA was isolated according to conventional methods from Arthrobacter spec. DSM 2563 (J.Marmur, J.Mol. Biol. 3, (1961) 208-218; S. Visuvanathan et al., J.Microbiol.Meth. 10 (1989) 59-64). The DNA isolated in this way was completely cleaved with the restriction enzymes EcoRI and HindIII. The commercially available vector pUC18 (Boehringer Mannheim GmbH) was also cleaved with EcoRI/HindIII and ligated with the DNA fragments from Arthrobacter. Competent E.coli ED 8654 cells (DSM 2102) were transformed with the resulting recombinant plasmids (instructions: Sambrook, Fritsch, Maniatis—Molecular Cloning. Second Edition 1.74 ff.). About 200 colonies per selection plate were obtained after selection on ampicillin. The identification of clones coding for CSHase was carried out by means of a colorimetric test described in EP-A 0 154 269 in which sarcosine oxidase, peroxidase, carbamoylsarcosine, 4-aminoantipyrine and tribromo-3-hydroxybenzoic acid in phosphate buffer pH 7.8 were added.

In this colorimetric test CSHase converts the added carbamoyl sarcosine into sarcosine, this is degraded by sarcosine oxidase to glycine formaldehyde and hydrogen peroxide.

The peroxidase converts the added colour substrates into a dark-violet dye with the aid of the hydrogen peroxide formed. The increase in absorbance is measured at 546 nm. Two positive clones were identified per 1000 colonies in the plate activity test.

EXAMPLE 2

Isolation of DNA coding for CSHase

The DNA from the positive clones was isolated after plating out the colonies on agar and resuspending the clones from these agar plates. Retransformation showed that an expression in E.coli occured for a short time, these plasmids had, however, a very high instability. The enzyme activity which could be detected in the plate activity test was rapidly lost. It was, however, possible to isolate a 5 kb EcoRI/HindIII DNA fragment from this plate lysate which contains the CSHase gene. When this DNA fragment was shortened to 2.5 kb by cleavage with the restriction enzymes KpnI and BamHI and cleaved further with EcoRI/SalI to 1.3 kb, stable clones resulted.

FIG. 1 shows the recombinant plasmid pCSHaseI obtained by cloning the 5 kb Arthrobacter DNA fragment in pUC18 and the stable plasmid pCSHaseIII which resulted by deletion.

EXAMPLE 3

Construction of the expression vector pBMP61

The DNA coding for CSHase was cloned into the vector pBT2a-1 (DSM 3148P). For this the creatinase gene was first deleted from pBT2a-1 by cleavage with AvaI. The ends of the resulting DNA fragments were made blunt using Klenow enzyme and the four nucleotide triphosphates. The CSHase gene was cut out of pCSHaseI using the restriction enzymes SalI and KpnI, it was made blunt with Klenow enzyme and the four nucleotide triphosphates and ligated with the 2.6 kb long AvaI fragment from pBT2a-1 to result in the recombinant plasmid pBMP61 (see FIG. 2).

EXAMPLE 4

Construction of the expression vector pBMP62

Plasmid pBMP61 still contains the lacUV5 promoter from plasmid pBT2a-1. This promoter is not necessary for the expression. pBT2a-1 was therefore cleaved with AatII and AvaI and the resulting 2.4 kb long AvaI/AatII fragment was made blunt using Klenow enzyme and the four nucleotide triphosphates. The resulting 2.4 kb long fragment with blunt ends was then ligated with the 1.2 kb long SalI/KpnI fragment from pCSHaseI which had also been blunt-ended to form plasmid pBMP62 (FIG. 3). This plasmid which codes for CSHase also contains ca. 373 bp of an Arthrobacter sequence in the 5' untranslated region of the CSHase gene which is shown in SEQ ID NO:3.

EXAMPLE 5

Expression of CSHase in E.coli

The plasmids pBMP61 or pBMP62 which codes for CSHase were transformed in E.coli ED 8654 (DSM 2102) (instructions: Sambrook, Fritsch, Maniatis—Molecular Cloning. Second Edition 1.74 ff.) and selected on ampicillin. After culturing the clones in 5 ml LB overnight, the cells were harvested and lysed with ultrasound and subsequently an activity test was carried out. The principle of measurement is the same as in the plate activity test of Example 1. The increase in absorbance is measured at a wavelength of 546 nm. The activity test is described in EP-A 0 154 269. A unit (U) is defined as $\mu$mol sarcosine formation per min at 25° C. under the measurement conditions in a coupled test with sarcosine oxidase and peroxidase.

An activity of 150 U/1×OD is obtained with the recombinant enzyme. This corresponds to an increase by a factor of ca. 50 compared to the original culture (Arthrobacter sp. DSM 2563).

| Strain | Activity [U/1 × OD] |
| --- | --- |
| Arthrobacter sp. DSM 2563 | 3 |
| E.coli | 0 |
| E.coli/pBMP61 | 150 |
| E.coli/pBMP62 | 150 |

EXAMPLE 6

Sequencing of the CSHase gene The 1.3 kb long Arthrobacter DNA fragment from pCSHaseIII which contains the CSHase gene was used to determine the DNA sequence. The DNA was subcloned in M13 and sequenced according to standard techniques (dideoxy method according to Sanger). An open reading frame results whose DNA sequence is shown in SEQ ID NO:1. It codes for a protein with 264 amino acids whose sequence is shown in SEQ ID NO:2.

---

We claim:

1. A recombinant DNA, comprising a sequence selected from the group consisting of a) SEQ ID NO: 1, b) a sequence corresponding to SEQ ID NO: 1 within the scope of the degeneracy of the genetic code and c) a sequence which hybridizes with a sequence from a) and/or b) under stringent hybridizing conditions wherein said sequence codes for a protein with N-carbamoyl sarcosine amidohydrolase activity and is not more than 1.3 kb long.

2. The recombinant DNA according to claim 1, wherein said sequence is selected from the group consisting of a) SEQ ID NO: 1 and b) a sequence which hybridizes with SEQ ID NO: 1 under stringent hybridizing conditions.

3. A recombinant vector, comprising a heterologous insertion selected from the group consisting of a) SEQ ID NO: 1, b) a sequence corresponding to SEQ ID NO: 1 within the scope of the degeneracy of the genetic code and c) a sequence which hybridizes with a sequence from a) and/or b) under stringent hybridizing conditions, wherein said sequence codes or a protein with N-carbamoyl sarcosine amidohydrolase activity, and wherein said heterologous insertion is not more than 1.3 kb long.

4. The recombinant vector according to claim 3, wherein said vector is a prokaryotic vector.

5. The recombinant vector according to claim 3, wherein said vector is a plasmid.

6. The recombinant vector according to claim 3, wherein the heterologous insertion is under the control of an inducible expression signal.

7. The recombinant vector according to claim 3, wherein the heterologous insertion is under the control of an expression signal which is heterologous to said vector.

8. The recombinant vector according to claim 7, wherein the expression signal is homologous to the heterologous insertion.

9. The recombinant vector according to claim 8, wherein the expression signal is an authentic promoter of a N-carbamoyl sarcosine amidohydrolase gene or a sequence derived therefrom.

10. The recombinant vector according to claim 3, wherein said heterologous insertion is selected from the group consisting of a) SEQ ID NO: 1 and b) a sequence which hybridizes with SEQ ID NO: 1 under stringent hybridizing conditions.

11. A cell transformed with the DNA according to claim 1.

12. A cell transformed with the vector according to claim 3.

13. The cell according to claim 11, wherein said cell is a bacterial cell.

14. The cell according to claim 13, wherein said cell is an *E. coli* cell.

15. A process for the isolation of a protein with N-carbamoyl sarcosine amidohydrolase activity, comprising the steps of
  a) transforming a cell with a DNA sequence or a vector containing such a DNA sequence wherein said DNA sequence is selected from the group consisting of a) SEQ ID NO: 1, b) a sequence corresponding to SEQ ID NO: 1 within the scope of the degeneracy of the genetic code and c) a sequence which hybridizes with a sequence from a) and/or b) under stringent hybridizing conditions, wherein said sequence codes for a protein with N-carbamoyl sarcosine amidohydrolase activity, and wherein the length of the DNA sequence is not more than 1.3 kb, to form a transformed host cell containing one or more copies of the DNA sequence,
  b) culturing the transformed hot cell in a suitable medium,
  c) expressing the DNA sequence in the transformed host cell and
  d) isolating any expression product from the medium or the host cell.

16. The process according to claim 15, wherein said host cell is *E. coli.*

17. The process according to claim 15, wherein the expression of the DNA sequence is under the control of an authentic promoter or a sequence derived therefrom.

* * * * *